(12) United States Patent
Bhat et al.

(10) Patent No.: US 6,706,013 B1
(45) Date of Patent: Mar. 16, 2004

(54) VARIABLE LENGTH DRUG DELIVERY CATHETER

(75) Inventors: Vinayak D. Bhat, Sunnyvale, CA (US); Steven B. Choi, Mountain View, CA (US); Paul M. Consigny, Sunnyvale, CA (US); Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 50 days.

(21) Appl. No.: 09/896,328

(22) Filed: Jun. 29, 2001

(51) Int. Cl.$^7$ ............................................. A61M 29/00
(52) U.S. Cl. .................... 604/96.01; 606/194; 606/101
(58) Field of Search ................... 606/194, 108; 604/53, 101, 102, 96.01, 194

(56) References Cited

U.S. PATENT DOCUMENTS

| 4,636,195 A | 1/1987 | Wolinsky ...................... 604/53 |
| 4,824,436 A | 4/1989 | Wolinsky ...................... 604/53 |
| 5,087,244 A | 2/1992 | Wolinsky et al. ............. 604/53 |
| 6,156,053 A | 12/2000 | Gandhi et al. .............. 606/194 |

*Primary Examiner*—Henry Bennett
*Assistant Examiner*—S Dagostino
(74) *Attorney, Agent, or Firm*—Paul J. Meyer, Jr.; Squire, Sanders & Dempsey, L.L.P.

(57) ABSTRACT

A catheter for insertion in a physiological lumen is provided which includes two balloons, wherein the distance between the balloons can be adjusted. The catheter can be used for the delivery of a therapeutic substance for the treatment of conditions such as restenosis.

19 Claims, 3 Drawing Sheets

VARIABLE LENGTH DRUG DELIVERY CATHETER

FIELD OF THE INVENTION

The present invention relates to a medical device for insertion into a physiological lumen. More specifically, the present invention relates to a balloon catheter for delivering a therapeutic substance to a blood vessel.

BACKGROUND

Increasingly, the diseases of the arteries are being treated with percutaneous interventions such as percutaneous transluminal angioplasty (PTA) instead of with vascular surgery. Percutaneous interventions are less invasive, cost efficient, and have lower risks. Typically during a PTA procedure, a catheter assembly having a balloon is introduced percutaneously into the cardiovascular system of a patient via the brachial or femoral artery. The catheter assembly is advanced through the vasculature until the balloon is positioned across an occlusive lesion. Once in position across the lesion, the balloon is inflated to a predetermined size to radially compress against the atherosclerotic plaque of the lesion to remodel the lumen. The balloon is then deflated to a smaller profile to allow the catheter to be withdrawn from the patient's vasculature.

Although PTA has proven to be an extremely effective procedure, many patients develop restenosis over the several months following the procedure, which may require another angioplasty procedure or a surgical by-pass operation. Restenosis is thought to involve the body's natural healing process. Angioplasty or other vascular,procedures injure the vessel walls, removing the vascular endothelium, disturbing the tunica intima, and causing the death of medial smooth muscle cells. Excessive neoinitimal tissue formation, characterized by smooth muscle cell migration and proliferation to the intima, follows the injury. Proliferation and migration of smooth muscle cells (SMC) from the media layer to the intima cause an excessive production of extra cellular matrices (ECM), which is believed to be one of the leading contributors to the development of restenosis. The extensive thickening of the tissues narrows the lumen of the blood vessel, constricting or blocking blood flow through the vessel.

To reduce the development of restenosis, therapeutic substances have been administered to the treatment site. For example, anticoagulant and antiplatelet agents are commonly used to inhibit the development of restenosis. In order to provide an efficacious concentration to the target site, systemic administration of such medication often produces adverse or toxic side effects for the patient. Local delivery is a preferred method of treatment in that smaller total levels of medication are administered in comparison to systemic dosages, but are concentrated at a specific site. Local delivery, thus, produces fewer side effects and achieves more effective results.

One technique for the local delivery of a therapeutic substance is through the use of porous balloons attached to a distal end of a catheter assembly. The expansion of the balloon, which in effect results in the dilation of the occluded region, is accomplished by injecting a therapeutic substance into the balloon. The use of a therapeutic substance as an expansion fluid additionally functions as a medicament for the diseased region, as the therapeutic substance is discharged from the porous balloon during and subsequent to the expansion therapy. Unfortunately, a shortcoming associated with this procedure is that the therapeutic substance is continuously carried off by the blood flow as it is being discharged into the vessel. The loss of the therapeutic substance from the treatment site results in an ineffective treatment of the target site and adverse exposure of the substance to healthy tissues.

Therefore, what is needed is a device that regulates blood flow in a treatment space in a physiological lumen, can deliver a therapeutic substance to the treatment space, and prolongs the residence time of the substance at the treatment space.

SUMMARY

In accordance with one aspect of the invention a medical device for insertion in a physiological lumen is provided. The medical device includes a catheter assembly having a first balloon element and a second-balloon element. The second balloon element is capable of being moved towards and away from the first balloon element to create a treatment space when the first and second balloon elements are inflated. A first port can be in fluid communication with the treatment space for supplying to or withdrawing from the created treatment space a therapeutic substance.

In accordance with one embodiment of the invention a second port is in fluid communication with the treatment space, wherein the second port is used for supplying to or withdrawing from the created treatment space the therapeutic substance. Accordingly, the first port can be used to withdraw a substance that is supplied from the second port.

The catheter assembly can include a first catheter tube supporting the first balloon element and a second catheter tube telescopically disposed over the first catheter tube and supporting the second balloon element. The first port can be disposed on the first catheter tube and in fluid communication with a lumen of the first catheter tube. The second catheter tube can include a central lumen for telescopically receiving the first catheter tube, wherein the inner diameter of the central lumen is sufficiently larger than the outer diameter of the first catheter tube so as to allow for the injection and withdrawal of a therapeutic substance from the gap between the surfaces.

In accordance with another aspect of the invention, a method for delivering a therapeutic substance to a physiological lumen is provided. The method comprises inserting a catheter assembly into a physiological lumen; positioning a first balloon element disposed on the catheter assembly at a target area within the physiological lumen; positioning a second balloon element relative to the first balloon element; inflating the first and second balloon elements to create a treatment space; and releasing a therapeutic substance through a first port of the catheter assembly in the treatment space. In one embodiment, the method further comprising removing the therapeutic substance through a second port of the catheter assembly.

DETAILED DESCRIPTION OF THE EMBODIMENTS

Figure 1:
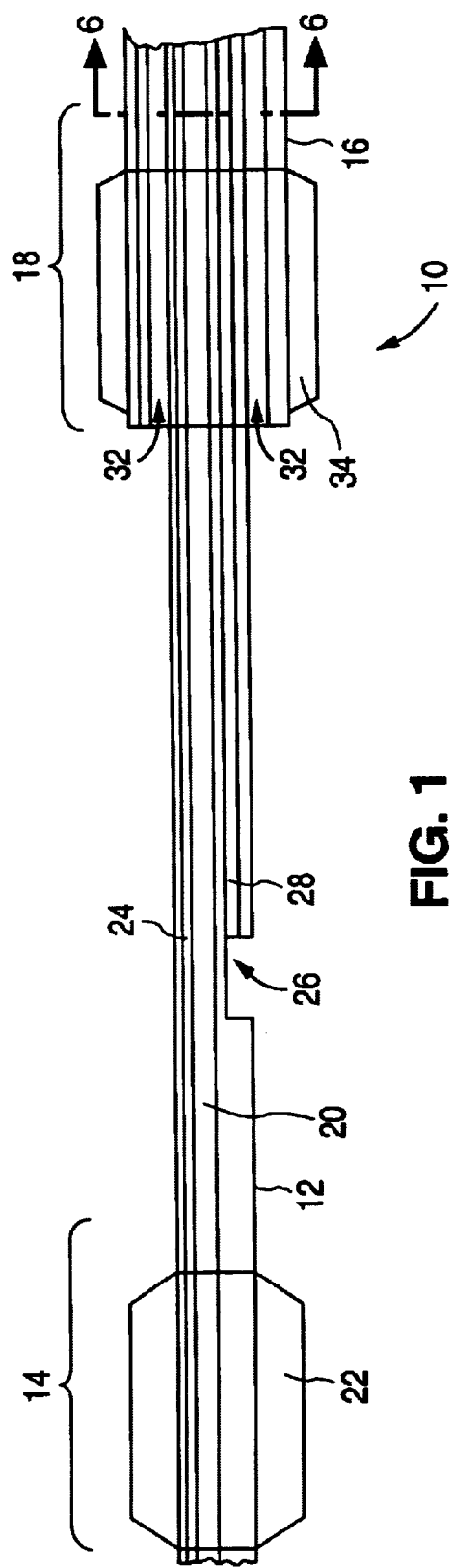
FIG. 1 is a partial cross sectional view of a catheter assembly.
Figure 2:
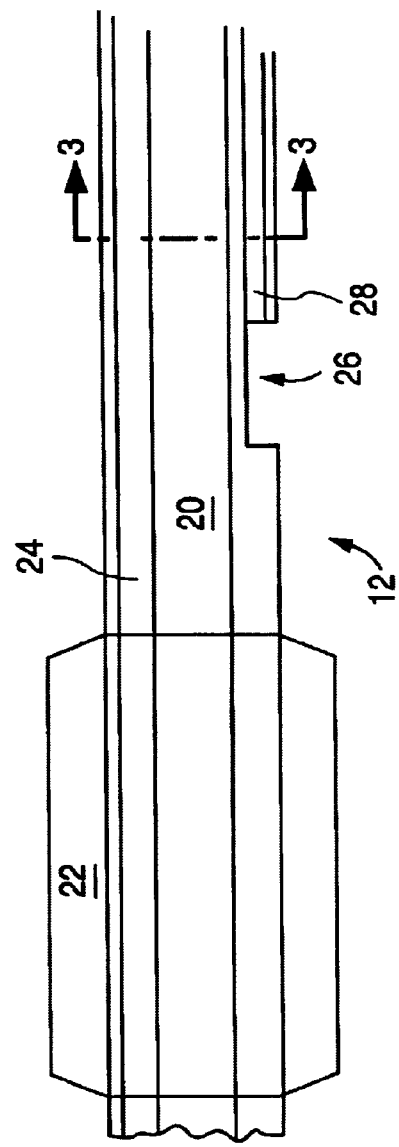
FIG. 2 is an enlarged partial cross sectional view of a first catheter tube for the catheter assembly.
Figure 3:
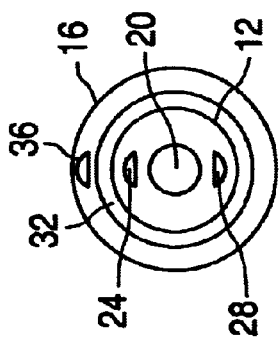
FIG. 3 is a cross-section taken along the line 3—3 of FIG. 2.

Referring now to the drawings, wherein similar parts are identified by like reference numerals, FIG. 1 illustrates a catheter assembly 10. Catheter assembly 10 is intended to broadly include any medical device designed for insertion into a physiological lumen to permit injection and/or withdrawal of fluids, to maintain the patency of the lumen, or for any other purpose. It is contemplated that the apparatus has applicability for use with any physiological lumen, including blood vessels, urinary tract, intestinal tract, kidney ducts, wind pipes, and the like. The catheter assembly is especially useful for inserting into peripheral arteries, such the superficial femoral artery.

Catheter assembly 10 includes a first catheter tube 12 having a proximal end (not illustrated) and distal end 14, and a second catheter tube 16, having a proximal end (not illustrated) and a distal end 18. The second catheter tube 16 is telescopically disposed over the first catheter tube 12.

The first catheter tube 12 can include a guidewire lumen 20 for allowing first catheter tube 12 to be fed over and maneuvered over a guidewire. A first balloon 22 is disposed on distal end 14. First balloon 22 is selectively inflatable to dilate from a collapsed configuration to a desired and controlled expanded configuration. First balloon 22 can be selectively inflated by supplying a fluid into a first inflation lumen 24 at a predetermined rate of pressure, for example 1–20 atm. First balloon 22 is also selectively deflatable, after inflation, to return to the collapsed configuration or a deflated profile. In one embodiment, first catheter tube 12 can include a port 26 in fluid communication with port lumen 28. Port 26 allows for injection or withdrawal of fluids through port lumen 28. Port 26 can be embodied by many different types of openings such as, but not limited to, holes, slits, annual gaps, porous membranes and osmotic filters.

Figure 5:
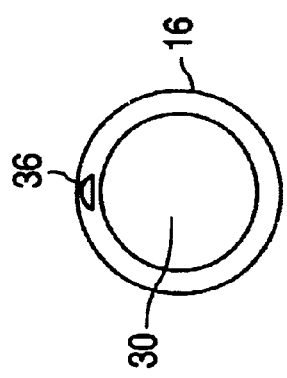
FIG. 5 is a cross-section taken along the line of 5—5 of FIG. 4.
Figure 6:
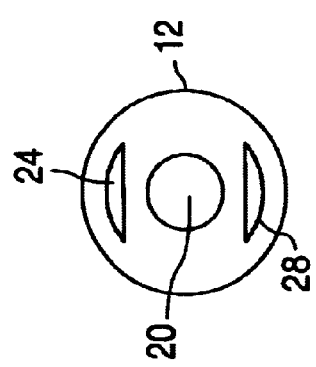
FIG. 6 is a cross-section taken along the line 6—6 of FIG. 1.
Figure 4:
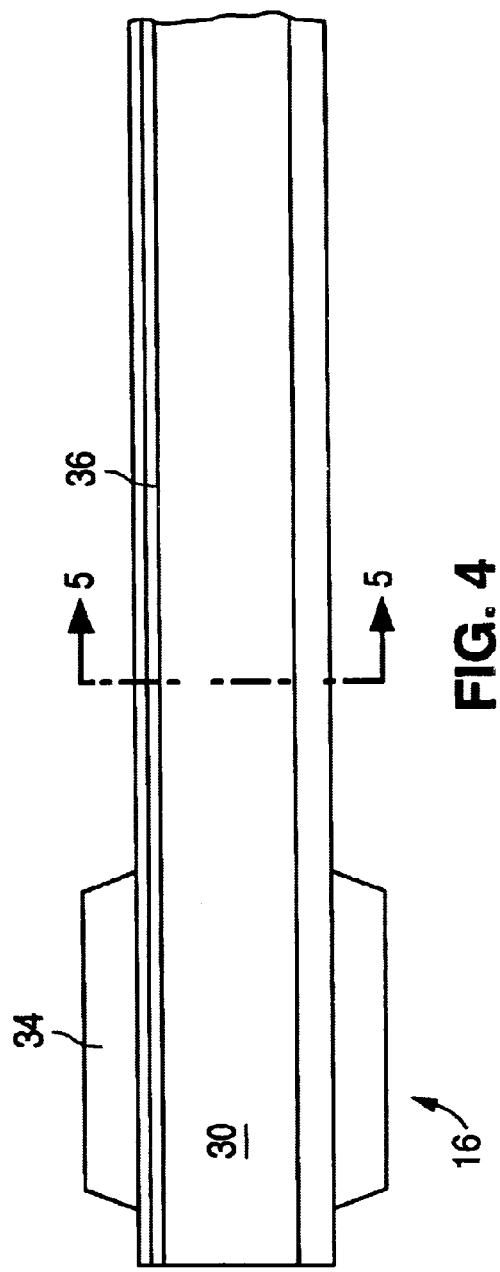
FIG. 4 is an enlarged partial cross sectional view of a second catheter tube for the catheter assembly.

Referring to FIGS. 4, 5, and 6, second catheter tube 16 includes a central lumen 30 sized so as to slidably receive first catheter tube 12, but large enough so as to create an annular gap 32 between the outer surface of first catheter tube 12 and the inner surface of central lumen 30. The space between the surfaces can be from about 0.25 mm to about 0.4 mm. Annular gap 32 functions as a second port which additionally allows for injection or withdrawal of fluids by a user. A second balloon 34 is disposed on distal end 18 and is in fluid communication with an inflation lumen 36. Second balloon 34 performs a similar function to that of first balloon 22 and can be sized to have the same outer diameter in the desired inflated state. The inflation of first and second balloons 22 and 34 create a treatment space for the application of a therapeutic substance. Annular gap 32 used in conjunction with port 26 can provide for the withdrawal of the bodily fluids, application of a therapeutic substance, and the re-circulation and application of the substance in the treatment space for maintaining the concentration of the therapeutic substance at a therapeutically acceptable level for a selected duration of time.

First and second balloons 22 and 34 can be made from any suitable material, including, but not limited to, polymers and copolymers of polyolefins, polyamides, polyesters and the like. The specific material employed must be mutually compatible with the fluids employed in conjunction with balloons 22 and 34 and must be able to stand the pressures that are developed therein. The balloons 22 and 34 can have any suitable thickness so long as the thickness does not compromise properties that are critical for achieving optimum performance. The properties include high burst strength, low compliance, good flexibility, high resistance to fatigue, the ability to fold, the ability to cross and recross a desired region of treatment or an occluded region in a lumen, and low susceptibility to defect caused by handling. By way of example, and not limitation, the thickness can be in the range of about 10 microns to about 30 microns, the diameters of balloons 22 and 34 in the expanded configuration can be in the range of about 2 mm to about 15 mm and the lengths can be in the range of about 3 mm to about 10 mm, the specific specifications depending on the procedure for which balloons 22 and 34 are to be used and the anatomy and size of the target lumen in which the balloons are to be inserted.

In accordance with another embodiment of the invention, first or second balloons 22 and 34 can also be used to deliver a therapeutic substance to the treatment space should either of balloons 22 and 34 be embodied so as to include a porous membrane. A therapeutic substance can be included in the fluid that is used to inflate balloons 22 or 34. To more effectively deliver a therapeutic substance to the treatment space, the balloon membrane can be exclusively porous on the portion of the membrane that faces the treatment space.

One of ordinary skill in the art can appreciate that any number of balloons can be included with the first or second catheter tubes 12 and 16. Such balloons can be strategically placed so as to serve their intended function, such as stent placement.

In another embodiment, an ultrasonic transducer and/or an electrode element (not shown) can be carried by catheter tube 12. Use of the ultrasonic transducer or electrode element is advantageous because tissue temperature and capillary and cellular permeability can be increased. These results can enhance intra-tissue transport of a substance, enhance cellular uptake, and cause vasodilation/relaxation, which may be beneficial in vascular applications. As is understood by one of ordinary skill in the art, an ultrasonic transducer can be barium titanate, lead zirconate titanate, or the like.

The active agent could be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site, improving the structural and elastic properties of the vascular site or to combat thrombosis. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic. antiallergic and antioxidant substances. Examples of such antineoplastics and/or antimitolics include paclitaxel (e.g. TAXOL® by Bristol-Myers Squibb Co., Stamford. Conn. docetanel (e.g. Taxotere®, from Aventis S.A., Frankfurt, Germany), methotrexate, azathioprinie, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co. Stamford, Conn.). Examples of such antiplatelets, anticoagulants, antifibrin, and antithrombins include sodium heparin, low molecular weight heparins, heparinoids, hirudin. argatroban, forskolin, vapiprost, prostacyclin and prostacyclin analogues, dextran, D-phe-pro-argchloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn. ) cilazapril or lisinopril (e.g. Prinivilo® and Prinzidez® from Merck & Co. Inc. Whitehouse Station. N.J.). calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as-those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alphainterferon, genetically engineered epithelial cells, rapamycin and dexamethasone. understood by one of ordinary skill in the art, an ultrasonic transducer can be barium titanate, lead zirconate titanate, or the like.

Figure 7A:
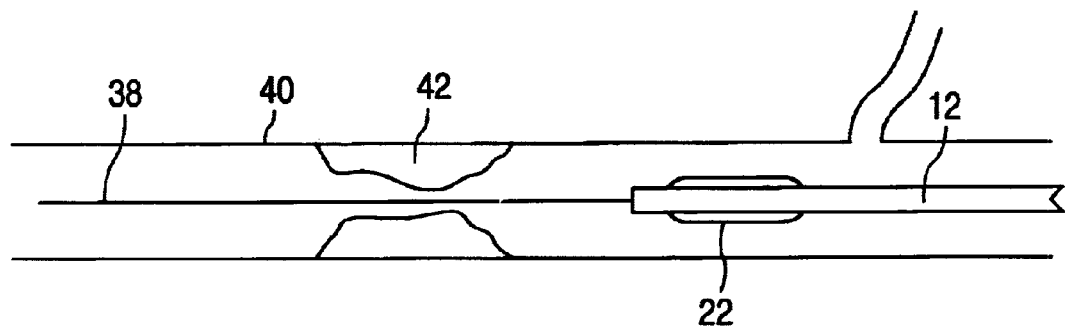
FIGS. 7A–7D illustrate an exemplary use of the catheter assembly.
Figure 7B:
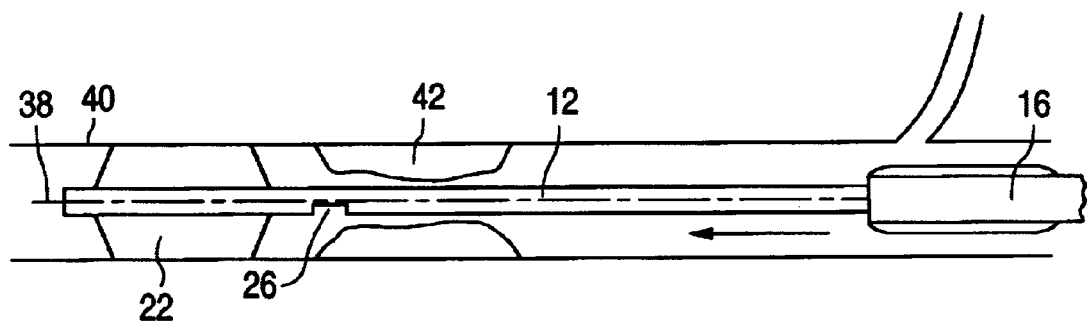
Figure 7C:
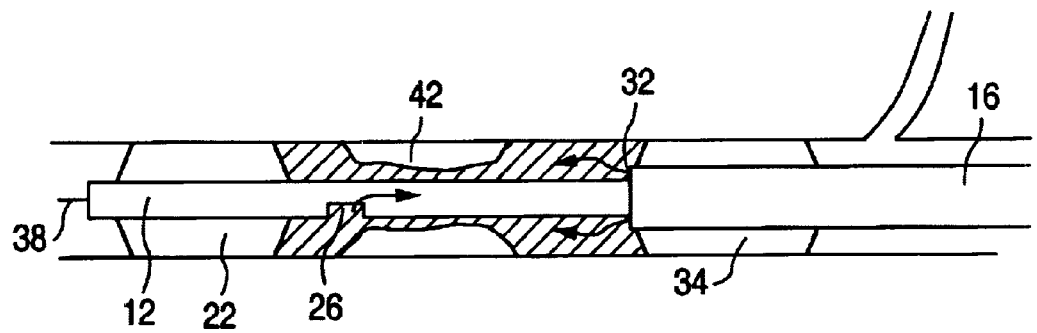

METHODS OF USE;

Once the treatment space is created a therapeutic substance can be delivered through either port 26 or 32, while the other port can be used for withdrawal of the therapeutic substance. Arrows of FIG. 7C illustrate port 32 being used for diffusion of the therapeutic substance and port 26 for suction of the substance out from the treatment zone. The combination of the two ports 26 and 32 can be used to maintain the concentration of the therapeutic substance at a therapeutically effective level. Since both of the inflated balloons 22 and 34 seal the area surrounding legion 42, the delivery of the therapeutic substance can take place under advantageous conditions. This allows the therapeutic substance to be delivered at a higher pressure and a greater concentration thereby increasing the efficiency of the uptake by the legion 42 or the surrounding vessel walls. Longer residence times for the therapeutic substances may be especially helpful for certain types of drugs like heparin which has significant antiproliferative properties at high concentrations. Studies suggest that heparin will work to reduce proliferating SMCs when the local concentration of heparin in the vessel wall is high (e.g., 1 microgram/cm$^2$ surface).

Figure 7D:
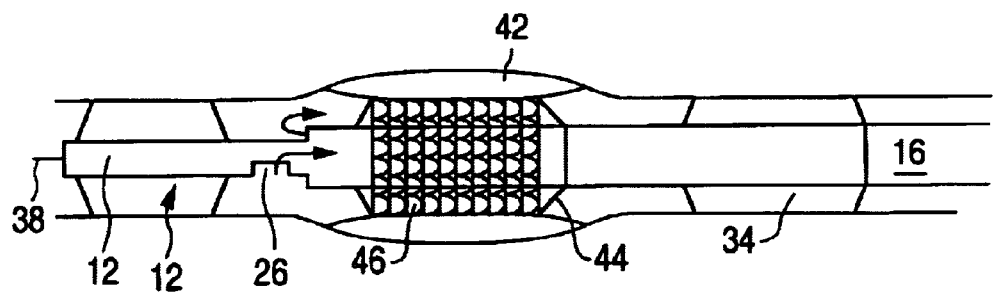

In accordance with another method, as illustrated in FIG. 7D, a third balloon 44 carrying a stent 46 can be used to support the vessel wall and/or deliver a therapeutic substance to the occluded region 42. Third balloon 44 can be disposed either on the first catheter tube 12 or the second catheter tube 16 and should be capable of being inflated independent of balloons 22 and 34. Stent 46 can be coated with a polymeric material impregnated with a therapeutic substance for sustained release of the substance. By way of example, stent 46 can be coated with polyethylene glycol and/or heparin.

While particular embodiments of the present invention have been shown and described, it will be obvious to those having ordinary skill in the art that changes and modifications can be made without departing from this invention in its broader aspects.

What is claimed is:

1. A medical device for insertion in a physiological lumen comprising:

a catheter assembly;

a first balloon element integrated with the catheter assembly;

a second balloon element integrated with the catheter assembly and capable of being nmoved towards and away from the first balloon element to create a treatment space when the first and second balloon elements are inflated; and a first port in fluid communication with the treatment space to supply to or withdraw from the created treatment space a therapeutic substance.

2. The device of claim 1, wherein the catheter assembly is adapted to be inserted into the superficial femoral artery.

3. The device of claim 1, additionally including a second port in fluid communication with the treatment space, wherein the second port is used to supply to or withdraw from the created treatment space the therapeutic substance.

4. The device of claim 1, further comprising a third balloon element integrated with the catheter assembly, the third balloon element carrying a balloon expandable stent.

5. The device of claim 1, wherein the catheter assembly comprises:

a first catheter tube including the first balloon element; and a second catheter tube disposed over the first catheter tube and including the second balloon element.

6. The device of claim 1, wherein the catheter assembly comprises:

a first catheter tube including the first balloon element, the first catheter tube having the first port disposed thereon; and a second catheter tube disposed over the first catheter tube and including the second balloon element.

7. The device of claim 1, wherein the catheter assembly comprises:

a first catheter tube including the first balloon element, the first catheter tube having the first port disposed thereon; and a second catheter tube including the second balloon element, the second catheter tube including a central lumen to receive the first catheter tube, wherein the inner diameter of the central lumen is sufficiently larger than the outer diameter of the first catheter tube so as to allow for the injection or withdrawal of a therapeutic substance from the gap between the surfaces.

8. A catheter assembly comprising:

a first catheter tube having a first lumen in fluid communication with a first balloon; and a second catheter tube having a first lumen in fluid communication with a second balloon and a second lumen for slidably receiving the first catheter tube, wherein the outer diameter of the first catheter tube is smaller than the inner diameter of the second lumen so as to create a port through which a therapeutic substance can be applied to or withdrawn from a treatment zone created between the first and second balloons in an inflated state.

9. The catheter assembly of claim 8, wherein the first catheter tube additionally includes a port in fluid communication with a second lumen of the first catheter tube for applying to or withdrawing from the treatment zone the therapeutic substance.

10. A method for delivering a therapeutic substance to a physiological lumen comprising:

inserting a catheter assembly into a physiological lumen;

positioning a first balloon element disposed on the catheter assembly at a target area within the physiological lumen;

positioning a second balloon element relative to the first balloon element;

inflating the first and second balloon elements to create a treatment space; and releasing a therapeutic substance through a first port of the catheter assembly in the treatment space.

11. The method of claim 10, wherein the act of releasing comprises injecting a therapeutic substance added to a fluid carrier into a lumen of the catheter assembly which is in fluid communication with the first port.

12. The method of claim 10, further comprising removing the therapeutic substance through a second port.

13. The method of claim 10, wherein the catheter assembly is inserted into a superficial femoral artery.

14. The method of claim 10, further comprising adjusting the position of the second balloon element relative to the first balloon element by moving the second balloon element towards or away from the first balloon element.

15. The method of claim 10, wherein the catheter assembly comprises:

a first catheter tube supporting the first balloon element, the first catheter tube having the first port disposed thereon; and a second catheter tube telescopically disposed over the first catheter tube and supporting the second balloon element.

16. The method of claim 10, wherein the catheter assembly comprises:

a first catheter tube supporting the first balloon element, the first catheter tube having the first port disposed thereon; and a second catheter tube supporting the second balloon element, the second catheter tube including a central lumen for telescopically receiving the first catheter tube, wherein the inner diameter of the central lumen is sufficiently larger than the outer diameter of the first catheter tube so as to allow for the injection or withdrawal of therapeutic substances from the space between the surfaces.

17. The device of claim 7, wherein the cap between the surfaces is from about 0.25 mm to about 0.4 mm.

18. The device of claim 8, wherein the port created between the first catheter tube and the second catheter tube is from about 0.25 mm to about 0.4 mm.

19. The method of claim 16, wherein the space between the surfaces is fron about 0.25 mm to about 0.4 mm.

* * * * *

UNITED STATES PATENT AND TRADEMARK OFFICE
CERTIFICATE OF CORRECTION

PATENT NO. : 6,706,013 B1
DATED : March 16, 2004
INVENTOR(S) : Bhat et al.

It is certified that error appears in the above-identified patent and that said Letters Patent is hereby corrected as shown below:

Column 6,
Line 16, change "nmoved" to -- moved --.

Column 7,
Line 22, change "of-releasing" to -- of releasing --.

Column 8,
Line 25, change "cap between" to -- gap between --.
Line 31, change "is fron" to -- is from --.

Signed and Sealed this

First Day of February, 2005

JON W. DUDAS
*Director of the United States Patent and Trademark Office*